United States Patent [19]
Darms et al.

[11] 4,127,712
[45] Nov. 28, 1978

[54] PHTHALIC ACID DIESTERS OR ESTER-AMIDES SUBSTITUTED BY ALKENYLAMINO GROUPS

[75] Inventors: Roland Darms, Therwil; Hubert Meindl, Riehen, both of Switzerland

[73] Assignee: Ciba-Geigy Corporation, Ardsley, N.Y.

[21] Appl. No.: 857,164

[22] Filed: Dec. 5, 1977

[30] Foreign Application Priority Data

Dec. 14, 1976 [CH] Switzerland .................. 15703/76

[51] Int. Cl.$^2$ .............. C08F 218/14; C08F 222/22; C08F 226/06; C07C 101/66
[52] U.S. Cl. ............................. 526/258; 526/305; 526/326; 560/19
[58] Field of Search ............... 260/78 UA; 526/258, 526/305, 326; 560/19

[56] References Cited

U.S. PATENT DOCUMENTS

| 3,450,678 | 6/1969 | Rogers et al. ............... 260/78 A |
| 3,547,770 | 12/1970 | Greenspan ..................... 526/326 |
| 3,562,223 | 2/1971 | Bargain et al. ............... 260/78 UA |
| 4,035,345 | 7/1977 | Ducloux et al. ............. 260/78 UA |
| 4,078,142 | 3/1978 | Keske .............................. 560/19 |

FOREIGN PATENT DOCUMENTS 4,873,207  3/1973  Japan ......................... 526/305

*Primary Examiner*—John Kight, III
*Attorney, Agent, or Firm*—Luther A. R. Hall

[57] ABSTRACT

Novel phthalic acid diesters or ester-amides substituted by alkenylamino groups, processes for their preparation and hot-curable mixtures which are stable on storage and contain at least one phthalic acid diester according to the invention or a phthalic acid ester-amide according to the invention and a polyimide which has at least two groupings containing a C=C double bond are described. These hot-curable mixtures which are stable on storage are distinguished by improved processing characteristics, in particular a prolonged pot life, and are suitable for the production of various mouldings and especially also for the production of complicated castings.

11 Claims, No Drawings

PHTHALIC ACID DIESTERS OR ESTER-AMIDES SUBSTITUTED BY ALKENYLAMINO GROUPS

The present invention relates to novel phthalic acid diesters or ester-amides substituted by alkenylamino groups, processes for their preparation and hot-curable mixtures which are stable on storage and contain at least one phthalic acid derivative according to the invention and a polyimide which has at least two groupings containing a carbon-carbon double bond.

Heat-curable resins which are obtained by a polyaddition reaction of a N,N'-bis-imide of an unsaturated dicarboxylic acid with primary diamines and the curing of these resins or pre-adducts by polymerisation by the action of heat are described in French Pat. No. 1,555,564. However, these resins are not suitable for the production of complicated castings since the starting mixtures of bis-imide and diamine must be heated in order to achieve an adequately low viscosity and the processing times are greatly shortened as a result.

Heat-curable compositions, for the production of mouldings, which contain a reaction product of a N,N'-bis-imide of an unsaturated dicarboxylic acid having two carbon-carbon double bonds, a polyamine and a further monomer having a carbon-carbon double bond which can be polymerised by heating are described in German Offenlegungsschrift No. 2,131,735. In these compositions, the last-mentioned monomer can also be, inter alia, an allyl derivative, for example an allyl ester, or an allyl ether, or an aromatic or heterocyclic compound containing an allyl substituent, especially allyl o-phthalate, allyl cyanurate or triallyl trimellitate. The said allyl compounds are apparently added in order to reduce the viscosity of the starting mixtures (bis-imide + polyamine). However, as a result mixtures are obtained which, because of the relatively short processing time, are not very suitable for the production of complicated castings, for filling cavities or gaps and for embedding bodies in so-called throw-away moulds. If it is desired to increase the time during which the compositions can be used in the molten, castable state, i.e. the processing time or the so-called pot life, it is necessary to add aromatic compounds having 2-4 benzene rings, as polymerisation regulators, in an amount of up to 10 percent by weight, relative to the composition of bis-imide, polyamine and monomer, so that a total of at least four different components is required for these heat-curable compositions.

The object of the invention was, therefore, to provide hot-curable mixtures which are stable on storage and have improved processing characteristics by a simpler route and avoiding the above disadvantages.

Accordingly, the invention relates to novel phthalic acid diesters and ester-amides of the formula I

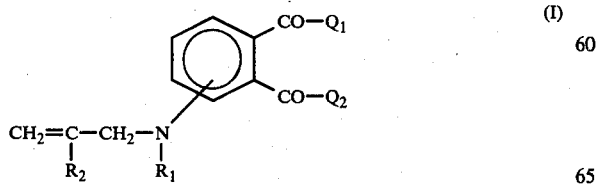

(I)

in which one of $Q_1$ and $Q_2$ is $-OR_3$ and the other is $-OR_4$ or

$R_1$ is hydrogen or

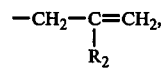

$R_2$ is hydrogen or methyl and $R_3$, $R_4$, $R_5$ and $R_6$ independently of one another are alkyl having 1–12 carbon atoms or alkenyl having 2–5 carbon atoms.

Using the phthalic acid diesters and ester-amides, according to the invention, of the formula I and polyimides which have at least two groupings containing a carbon-carbon double bond, it is possible, surprisingly, without the addition of polymerisation regulators or the like, to prepare hot-curable mixtures which are stable on storage and which, without a perceptible impairment of their viscosity or of the mechanical and electrical properties of the products which can be produced therefrom, have an adequately long processing time, so that they can also be used for the production of complicated castings.

The phthalic acid diesters and ester-amides, according to the invention, of the formula I can be prepared by reacting a compound of the formula II

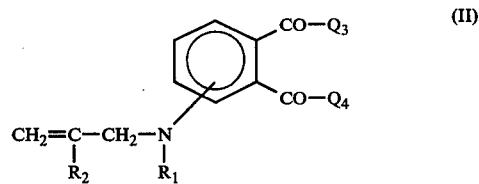

(II)

in the presence of an inorganic or organic base with an alcohol of the formula III $$HO-R_4 \quad \text{(III)}$$

to give a compound of the formula IV

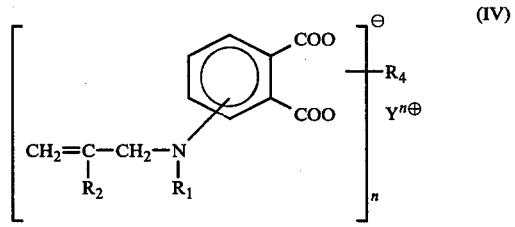

(IV)

and then allowing the compound of the formula IV to react with an amine of the formula V

(V)

and/or a compound of the formula VI $$X-R_3 \quad \text{(VI)}$$

In the above formulae II–VI, $R_1$, $R_2$, $R_3$, $R_4$, $R_5$ and $R_6$ are as defined under formula I, one of $Q_3$ and $Q_4$ is —OH and the other is —OH or —O$^-$M$^+$, or $Q_3$ and $Q_4$ together form the grouping —O—, Y is the cation of an inorganic or organic base, X is a chlorine or bromine atom or the grouping —O—SO$_2$—O—R$_3$, M$^+$ is an alkali metal cation, a trialkylammonium cation having 3–24, and especially 3–12, carbon atoms or a quaternary ammonium cation and n is the number 1 or 2.

If desired, the resulting phthalic acid diesters or ester-amides can then be converted into other derivatives of the formula I by transesterification.

Phthalic acid ester-amides of the formula Ia

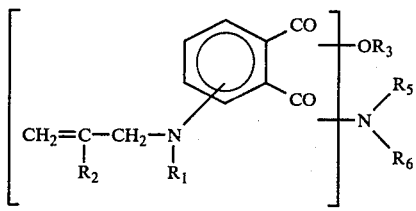
(Ia)

can also be prepared by reacting a compound of the formula II with an amine of the formula V to give a compound of the formula VII

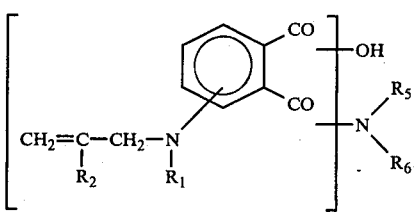
(VII)

and then allowing the compound of the formula VII to react in the presence of an inorganic or organic base with a compound of the formula VI.

In the above formulae Ia and VII, $R_1$, $R_2$, $R_3$, $R_5$ and $R_6$ are as defined under formula I.

Finally, compounds of the formula I can also be prepared by reacting a compound of the formula VIII

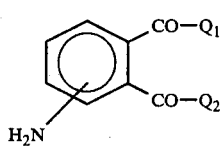
(VIII)

with a compound of the formula IX

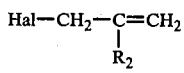
(IX)

in which formulae $Q_1$, $Q_2$ and $R_2$ are as defined under formula I and Hal is a halogen atom, especially chlorine or bromine.

Alkyl or alkenyl groups represented by $R_3$ to $R_6$ can be straight-chain or branched. Possible alkyl groups $R_3$ to $R_6$ are, especially, alkyl groups having 1–8 and in particular 1–4 carbon atoms. Examples of such groups which may be mentioned are: the methyl, ethyl, n-propyl, isopropyl, n-butyl, sec.-butyl, tert.-butyl, n-pentyl, n-hexyl, n-octyl, n-decyl and n-dodecyl group. If $R_3$ to $R_6$ are alkenyl groups, these groups are preferably the methallyl group and especially the allyl group. $R_3$ and $R_4$, or $R_3$, $R_5$ and $R_6$, preferably have the same meaning.

If one of $Q_3$ and $Q_4$ is a group —O$^-$M$^+$, M$^+$ is, for example, the lithium, sodium, potassium, trimethylammonium, triethylammonium, methyl-diethylammonium or tri-n-octylammonium cation. Examples of quaternary ammonium cations M$^+$ are the benzyltrimethylammonium and the tetramethylammonium cation. M$^+$ is preferably the sodium cation.

$R_1$ is preferably —CH$_2$—CH=CH$_2$, whilst $R_2$ is especially hydrogen.

Inorganic or organic bases which can be employed in the reaction of a compound of the formula II with an alcohol of the formula III or in the reaction of a compound of the formula VII with a compound of the formula VI are, for example, tertiary amines, pyridine, alkaline earth metal carbonates, hydroxides or alcoholates having 1–4 carbon atoms in the alkyl part and alkali metal carbonates, hydroxides or alcoholates having 1–4 carbon atoms in the alkyl part, such as trimethylamine and triethylamine, pyridine, magnesium carbonate, calcium carbonate, potassium carbonate and sodium carbonate, lithium hydroxide, potassium hydroxide and sodium hydroxide, magnesium methylate, potassium ethylate and sodium ethylate, potassium tert.-butylate and sodium tert.-butylate. Preferred bases are triethylamine and sodium alcoholates or potassium alcoholates, depending on the reactants. Alkaline earth metal alcoholates and alkali metal alcoholates can also be formed in situ when reacting a compound of the formula II with an alcohol of the formula III if an excess of the corresponding alcohol is employed. Y$^\oplus$ is, accordingly, preferably HN$^\oplus$—(CH$_3$)$_3$, HN$^\oplus$—(C$_2$H$_5$)$_3$, Na$^\oplus$ or K$^\oplus$ (n = 1).

The

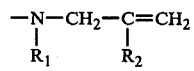

groupings are preferably in the orthoposition relative to the —COQ$_1$ or —COQ$_2$ group. The phthalic acid diesters and ester-amides according to the invention, and also the corresponding starting materials of the formula II can, however, also be employed in the form of mixtures of the 3- and 4-isomers.

Preferred compounds of the formula I are those in which $R_1$ is —CH$_2$CH=CH$_2$, $R_2$ is methyl and especially hydrogen and $R_3$ and $R_4$ are each alkyl having 1–8, and especially 1–4, C atoms or allyl, or $R_3$, $R_5$ and $R_6$ independently of one another are alkyl having 1–4 C atoms or allyl.

Particularly preferred compounds of the formula I are those in which $R_1$ is —CH$_2$CH=CH$_2$, $R_2$ is hydrogen and $R_3$ and $R_4$ are each alkyl having 1–8, and especially 1–4, C atoms or allyl, or $R_3$ is alkyl having 1–4 C atoms or allyl and $R_5$ and $R_6$ are each allyl.

The starting compounds of the formula II and the intermediates of the formulae IV and VII are novel. The compounds of the formula II can be prepared by reacting aminophthalic acid derivatives of the formula X

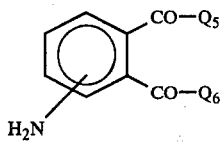

with a compound of the formula IX to give a phthalic acid derivative of the formula II′

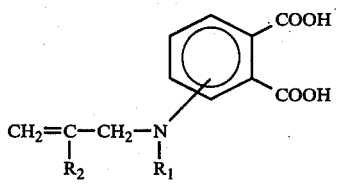

and, if desired, converting the resulting phthalic acid of the formula II′ into another derivative of the formula II, for example to the corresponding anhydrides by subsequent chemical cyclisation or cyclisation by the action of heat, or to the corresponding mono-salts by reaction with suitable bases, such as NaOH, according to methods which are known per se.

In the above formulae X and II′, $Q_5$ and $Q_6$ independently of one another are —OH or a group —O$^-$M$^+$ and M$^+$, $R_1$ and $R_2$ are as defined under formulae I and II.

The starting compounds of the formulae III, V, VI, VIII and IX are known or can be prepared according to methods which are known per se. Aminophthalic acid derivatives of the formula VIII can be obtained, for example, by catalytic hydrogenation from the corresponding nitro compounds in which $R_3$, $R_4$, $R_5$ and/or $R_6$ = alkyl having 1–12 carbon atoms and, if desired, subsequent transesterification to allyl derivatives according to the definition.

The starting materials of the formula II which are used are preferably the corresponding anhydrides.

The reactions described above are appropriately carried out in an inert organic solvent at temperatures between about 20° and 120° C., preferably between about 30° and 100° C. Suitable inert organic solvents are, for example, aromatic hydrocarbons, such as benzene, toluene or xylenes; aliphatic and cyclic ethers, such as diethyl ether, tetrahydrofurane, tetrahydropyrane and dioxane; dialkylsulphoxides, such as dimethylsulphoxide and diethylsulphoxide; N,N,N′,N′-tetramethyl-urea and tetrahydrothiophene dioxide (sulpholane). In the case of the reaction of a compound of the formula II with an alcohol of the formula III, an excess of the corresponding alcohol can also serve as the solvent.

If one of $Q_3$ and $Q_4$ in formula II is a group —O$^-$M$^+$, the reaction is appropriately carried out in the presence of a dehydrating agent which does not have an acid reaction, such as dicyclohexylcarbodiimide. The reaction of a compound of the formula VIII with a halide of the formula IX is appropriately carried out in the presence of an acid-binding agent, such as tertiary amines, for example trimethylamine or triethylamine.

After the reaction has ended, the compounds of the formula I are isolated and purified in a conventional manner, for example by filtering and distilling.

The invention also relates to hot-curable mixtures which are stable on storage and contain (a) at least one phthalic acid diester or one phthalic acid ester-amide of the formula I, (b) at least one polyimide which has, per molecule, at least two radicals of the formula XI

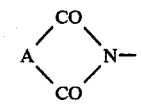

in which A is a divalent radical containing a carbon-carbon double bond, and, if appropriate, (c) a polymerisation initiator and to a process for the preparation of crosslinked polymers containing imide groups by reacting at least one phthalic acid diester or one phthalic acid ester-amide of the formula I and at least one polyimide according to the definition with one another, if appropriate in the presence of a polymerisation initiator.

Most of the polyimides which can be employed according to the invention are described in the literature; c.f. for example, British patent specification No. 1,066,390, U.S. Pat. No. 3,528,950, French Pat. No. 1,555,564 and German Offenlegungsschriften Nos. 2,230,874 and 2,350,471.

Bis-imides of the formula XII

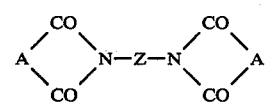

in which Z is a divalent bridge member having 2–30 carbon atoms and A is

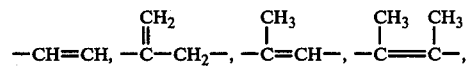

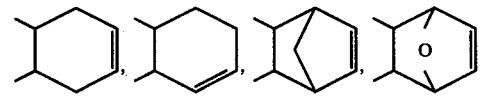

and especially

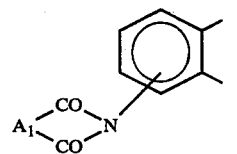

in which $A_1$ can have the same meanings as A with the exception of the last-mentioned meaning are preferred.

Particularly preferred compounds are those of the formula XII in which A is a group of the formula —CH=CH—,

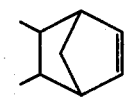

and especially

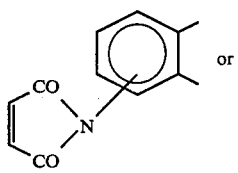 or

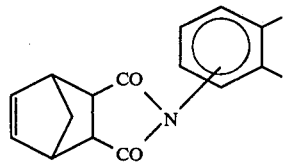

and Z is a 4,4'-diphenylmethane or 4,4'-diphenyl ether radical.

Possible bridge members Z are, especially, alkylene groups having 2-12 and especially 2-6 carbon atoms, phenylene or naphthylene groups which are unsubstituted or substituted by halogen atoms, such as chlorine, fluorine or bromine, or by alkyl or alkoxy groups having 1-4, and especially 1 or 2, carbon atoms, cyclohexylene groups and groups of the formulae

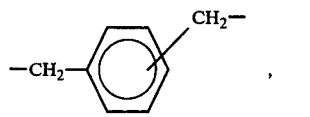

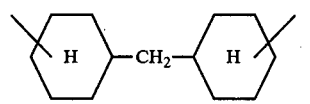

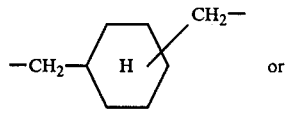 or

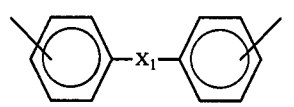

in which $X_1$ is —$CH_2$—, —O—, —S—, —SO—, —$SO_2$— or

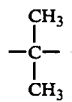

However, oligoimides of the type described in German Offenlegungsschrift No. 2,230,874, or bis- and tris-imides of the formula XIII

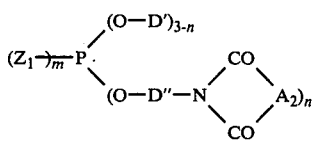 (XIII)

can also be employed in the mixtures according to the invention. In formula XIII, D' and D" are aromatic radicals which are unsubstituted or substituted or interrupted by an oxygen atom, an alkylene group or a sulphonyl group, $Z_1$ is an oxygen or sulphur atom, m is the number 1 or 0 and n is the number 2 or 3 and $A_2$ is a radical of the formulae $$-CH-CH-, \quad -\overset{CH_3}{\underset{|}{C}}=CH-, \quad -\overset{CH_2}{\underset{||}{C}}-CH_2- \text{ or}$$

$$-\overset{CH_3}{\underset{|}{C}}=\overset{CH_3}{\underset{|}{C}}-.$$

Examples of suitable polyimides which may be mentioned are: N,N'-ethylene-bis-maleimide, N,N'-hexamethylene-bis-nadicimide, N,N'-m- or -p-phenylene-bis-maleimide, N,N'-p-tolylene-bis-maleimide, N,N'-p-cyclohexylene-bis-1,2,3,6-tetrahydrophthalimide, N,N'-m- or -p-xylylene-bis-citraconimide, N,N'-hexamethylene-bis-3,6-endoxo-1,2,3,6-tetrahydrophthalimide, N,N',4,4'-dicyclohexylmethane-bis-maleimide, N,N',4,4'-diphenylmethane-bis-nadicimide, N,N',4,4'-diphenylmethane-bis-maleimide, N,N',4,4'-(diphenyl ether)-bis-maleimide, N,N',4,4'-diphenylsulphone-bis-maleimide, N,N',α,β',4,4'-dimethylenecyclohexane-bis-maleimide, N,N',4,4'-diphenylcyclohexane-bis-maleimide, N,N',4,4',2,2-diphenylpropane-bis-maleimide, N,N',γ,γ'-1,3-dipropylene-5,5-dimethyl-hydantoin-bis-maleimide, N,N',4,4'-diphenylmethane-bis-dimethyl-maleimide, N,N'-hexamethylene-bis-dimethylmaleimide, N,N',4,4'-diphenylmethane-bis-3-maleimidylphthalimide, N,N',4,4'-(diphenyl ether)-bis-3-nadicimidylphthalimide, N,N',4,4'-diphenylsulphone-bis-4-maleimidylphthalimide, the N,N'-bis-maleimide of 4,4'-diaminotriphenyl phosphate or of 4,4'-diaminotriphenyl thiophosphate and the N,N',N"-tris-maleimide of tris-(4-aminophenyl) phosphate.

Polyimides according to the definition can be obtained by methods which are known per se by reacting suitable diamines or polyamines with anhydrides of the formula (XIV)

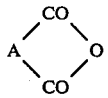 (XIV)

in which A is as defined.

Mixtures of two or more polyimides according to the definition and/or mixtures of different compounds of the formula I can also be used according to the invention.

The molar ratio of the compound of the formula I to the polyimide according to the definition can vary within wide limits. Mixtures containing up to 50 mol percent, and preferably 5-30 mol percent, of a compound of the formula I are appropriately used.

Depending on the intended use, cationic, anionic or free radical polymerisation initiators which are known per se can also be used to the mixtures according to the invention. In general, these polymerisation initiators are used in an amount of about 0.01 to 5 percent by weight, and preferably of 0.01 to 1.5 percent by weight, relative to the total weight of the reactants. Free radical initiators, such as inorganic or organic peroxides or azo compounds, for example hydrogen peroxide, potassium peroxydisulphate, tert.-butyl hydroperoxide, di-tert.-butyl peroxide, peracetic acid, benzoyl peroxide, diacyl peroxides, cumene hydroperoxide, tert.-butyl perbenzoate, tert.-alkyl peroxycarbonates and α,α'- azoisobutyronitrile, are preferred. In general, however, the addition of polymerisation initiators can be omitted.

The compounds of the formula I and the polyimides according to the definition are preferably reacted with one another in the melt or partly in the melt and partly in the solid phase. However, the reaction can also be carried out in solution. In most cases, however, the addition of organic solvents is superfluous because the starting mixtures as such already have an adequately low viscosity at temperatures above about 160° C. The reaction in the melt is appropriately carried out at temperatures between about 150° and 250° C. and preferably between 160° and 200° C.

Suitable organic solvents which can be used for the reaction in solution are, for example, dioxane, tetrahydrofurane, tetramethylurea, dimethylformamide, dimethylacetamide and N-methylpyrrolidone.

Processing of the mixtures according to the invention to give crosslinked polymers containing imide groups can also be carried out in two stages. After mixing and, where appropriate, after subsequent grinding of the starting materials, the powder or the liquid is first heated to about 150°–220° C. for a limited period. During this period, a soluble prepolymer forms which is still thermoplastic. If desired, this prepolymer is again ground to a powder before further processing. However, the prepolymerisation can also be carried out by heating a solution or suspension of the starting materials in one of the abovementioned organic solvents. Subsequently, the prepolymers are finally cured by heating to temperatures between about 170° and 250° C.

The production of the crosslinked polymers containing imide groups is as a rule effected with simultaneous shaping to give mouldings, sheet-like structures, laminates, glue bonds, foams and the like. The additives commonly used in the technology of curable plastics, such as fillers, plasticisers, pigments, dyes, mould release agents and flame-retardant substances, can be added to the curable mixtures. Fillers which can be used are, for example, glass fibres, mica, graphite, quartz powder, kaolin, colloidal silicon dioxide or metal powders. Substances which can be used as mould release agents are, for example, silicone oil, various waxes, zinc stearate or calcium stearate and the like.

Shaping of the products which can be produced with the mixtures according to the invention can be effected in a very simple manner by the casting process using conventional casting moulds.

However, shaping can also be carried out by the hot pressing process using a press at temperatures between about 170° and 250° C. and under a pressure of about 100–450 kp/cm².

The polymers which can be produced with the mixtures according to the invention can be employed, in particular, in the fields of casting production, surface protection, the electrical industry, laminating processes, adhesives and foam production and in the building trade.

EXAMPLE 1

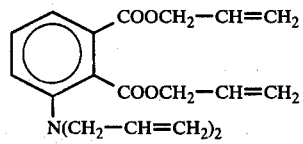

11.6 g (0.2 mol) of allyl alcohol and 20.3 g (0.2 mol) of triethylamine are added successively to a solution of 24.3 g (0.1 mol) of 3-N,N-diallylaminophthalic anhydride in 50 ml of toluene. The mixture is stirred at about 60° C. for 30 minutes and 24.2 g (0.2 mol) of allyl bromide are then added dropwise. After the exothermic reaction has subsided, the reaction mixture is stirred for a further 1 hour at 50°–60° C. and is then cooled to 20° C. and the dissolved product is separated by filtration from the triethylammonium bromide which has precipitated. Subsequently, the toluene is first distilled off and the oily residue is then purified by vacuum distillation. This gives 27.6 g (81% of theory) of 1,2-diallyl-3-N,N-diallylaminophthalate; boiling point under 0.01 mm: 143°–145° C.

Analysis for $C_{20}H_{23}NO_4$: calculated — C 70.4%, H 6.8%, N 4.1%; found — C 70.6%, H 6.9%, N 4.4%.

The 3-N,N-diallylaminophthalic anhydride used in the above example is prepared as follows: 225 g (1.0 mol) of disodium 3-aminophthalate and 138 g (1.0 mol) of potassium carbonate are dissolved in 400 ml of water. 317.2 g (2.6 mols) of allyl bromide are added to the solution at about 25° C. and the reaction mixture is stirred for 4 hours at 30°–35° C. Diallylaminophthalic acid is precipitated by adding 200 ml of 35% strength aqueous hydrochloric acid. The product is filtered off at 10° C., washed with 100 ml of water and dried. Yield: 222 g = 85% of theory. 261 g (1 mol) of this 3-diallylaminophthalic acid are heated to 150°–155° C. A melt forms and this is stirred for 2 hours at about 150° C. while a stream of nitrogen is passed over and is then allowed to cool to 50° C. 750 ml of toluene and 750 ml of n-hexane are then added and the crude product is recrystallised from this mixture. This gives 237 g (95% of theory) of 3-N,N-diallylaminophthalic anhydride; melting point 94°–95° C.

EXAMPLE 2

If, in Example 1, the 24.3 g of 3-N,N-diallylaminophthalic anhydride are replaced by the same amount of 4-N,N-diallylaminophthalic anhydride and in other respects the procedure is identical, this gives the diallyl ester of 4-N,N-diallylaminophthalic acid; boiling point under 0.01 mm: 156°–159° C.

Analysis for $C_{20}H_{23}NO_4$: calculated — C 70.4%, H 6.8%, N 4.1%; found — C 70.3%, H 6.9%, N 4.3%.

If, in Example 1, the equimolecular amount of a mixture of 3- and 4-N,N-diallylaminophthalic anhydride is used in place of the 24.3 g of 3-N,N-diallylaminophthalic anhydride, this gives the corresponding mixture of isomers consisting of 1,2-diallyl 3-N,N-diallylaminophthalate and 1,2-diallyl 4-N,N-diallylaminophthalate.

EXAMPLE 3

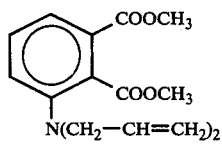

24.3 g (0.1 mol) of 3-N,N-diallylaminophthalic anhydride are introduced into a solution of 2.3 g (0.1 mol) of sodium in 100 ml of methanol. The reaction mixture is stirred for 30 minutes at 40°–45° C. and 37.8 g (0.3 mol) of dimethyl sulphate are then added. After stirring for 3 hours at 70°–75° C., the solution is cooled to 20°–25° C., the sodium methosulphate which has precipitated is filtered off and the solvent is distilled off from the filtrate. The residue is distilled in vacuo. This gives 25.8 g (89% of theory) of dimethyl 3-N,N-diallylaminophthalate; boiling point under 0.4 mm: 134°–138° C.

Analysis for $C_{16}H_{19}NO_4$: calculated — C 66.4%, H 6.6%, N 4.8%; found — C 66.4%, H 6.6%, N 4.9%.

EXAMPLE 4

14.5 g (0.05 mol) of dimethyl 3-N,N-diallylaminophthalate are introduced into a solution of 0.46 g (0.02 mol) of sodium in 100 ml of 1-octanol (the reagent, which is employed in a large excess, at the same time serves as the solvent). The mixture is stirred for 2 hours at 80°–90° C. and then for a further 2 hours at 110° C. The methanol which is liberated during the transesterification is distilled off continuously. The reaction mixture is then cooled to 20°–25° C. and dissolved in 250 ml of diethyl ether and the ethereal solution is extracted by shaking with three times 200 ml of a 5% strength aqueous solution of sodium chloride. The organic phase is dried over sodium sulphate and the diethyl ether is evaporated off after which the excess 1-octanol is distilled off in vacuo. For purification, the di-n-octyl 3-N,N-diallylaminophthalate can be distilled in vacuo.

Yield: 20 g (82.5% of theory) of di-n-octyl 3-N,N-diallylaminophthalate; boiling point under 0.01 mm, 197°–201° C.

Analysis for $C_{30}H_{47}NO_4$: calculated — C 74.2%, H 9.8%, N 2.9%; found — C 74.4%, H 9.8%, N 2.9%.

EXAMPLE 5

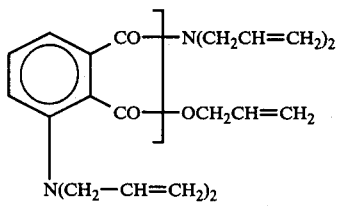

10.6 g (0.11 mol) of diallylamine are added to a solution of 24.3 g (0.1 mol) of 3-N,N-diallylaminophthalic anhydride in 200 ml of toluene. The mixture is stirred for 2 hours at 80°–85° C. and cooled to 50°–55° C. and 13.1 g (0.13 mol) of triethylamine and 15.7 g (0.13 mol) of allyl bromide are then added successively. The reaction mixture is stirred at 50°–60° C. for 3 hours. The salt formed during the reaction is removed by filtration. The toluene is removed from the mother liquor in a rotary evaporator and the oily residue is purified by vacuum distillation. This gives 31.5 g (83% of theory) of a mixture of the 1-diallylamide of 2-allyl-3-N,N-diallylaminophthalate and the 2-diallylamide of 1-allyl-3-N,N-diallylaminophthalate; boiling point under 0.04 mm, 162°–165° C.

Analysis for $C_{23}H_{28}NO_3$: calculated — C 72.6%, H 7.4%, N 7.4%; found — C 73.0%, H 7.4%, N 7.6%.

EXAMPLE 6

If, in Example 5, the 15.7 g of allyl bromide are replaced by 37.8 g (0.3 mol) of dimethyl sulphate and in other respects the procedure is as described in the said example this gives a mixture of the 1-diallylamide of 2-methyl 3-N,N-diallylaminophthalate and the 2-diallylamide of 1-methyl 3-N,N-diallylaminophthalate; boiling point under 0.1 mm = 180°–185° C.

Analysis for $C_{21}H_{26}NO_3$: calculated — C 71.1%, H 7.4%, N 7.9%; found — C 70.7%, H 7.4%, N 7.7%.

EXAMPLE 7

If, in Example 5, the 10.6 g of diallylamine are replaced by 10.8 g (0.11 mol) of di-n-propylamine and the 15.7 g of allyl bromide are replaced by 37.8 g (0.3 mol) of dimethyl sulphate, this gives a mixture of the 1-di-n-propylamide of 2-methyl 3-N,N-diallylaminophthalate and the 2-di-n-propylamide of 1-methyl 3-N,N-diallylaminophthalate; boiling point under 0.02 mm, 145°–155° C.

Analysis for $C_{21}H_{30}N_2O_3$: calculated — C 70.3%, H 8.4%, N 7.8%; found — C 70.0%, H 8.3%, N 7.6%.

EXAMPLE 8

14.8 g (0.2 mol) of n-butyl alcohol and 20.3 g (0.2 mol) of triethylamine are added successively to a solution of 27.1 g (0.1 mol) of 3-N,N-dimethallylaminophthalic anhydride in 50 ml of toluene. The mixture is stirred for 30 minutes at about 60° C. and 24.2 g (0.2 mol) of allyl bromide are then added dropwise. After the exothermic reaction has subsided, the mixture is stirred for a further 1 hour at 50°–60° C. and then cooled to 20° C. and the dissolved product is separated by filtration from the triethylammonium bromide which has precipitated. Subsequently, the toluene is first distilled off and the oily residue is then purified by vacuum distillation. This gives 29.6 g (77% of theory) of a mixture of 1-n-butyl 2-allyl 3-N,N-dimethallylaminophthalate and 2-allyl 1-n-butyl 3-N,N-dimethallylaminophthalate;

Analysis for $C_{23}H_{31}NO_4$: calculated — C 71.7%, H 8.1%, N 3.6% found — C 71.4%, H 7.9%, N 3.9%.

The 3-N,N-dimethallylaminophthalic anhydride used in the above example can be prepared as follows: 225 g (1.0 mol) of disodium 3-aminophthalate and 138 g (1.0 mol) of potassium carbonate are dissolved in 400 ml of water. 271.5 g (3.0 mols) of methallyl chloride are added to the solution at about 25° C. and the reaction mixture is stirred for 8 hours at 70°–75° C. 3-N,N-Dimethylallylphthalic acid is precipitated by adding 200 ml of 35% strength aqueous hydrochloric acid and is converted into 3-N,N-dimethallylaminophthalic anhydride in the manner described in Example 1.

EXAMPLE 9

19.33 g (0.054 mol) of 4,4'-bis-maleimidyl-diphenylmethane (BMDM) and 2.91 g (0.006 mol) of the di-n-octyl 3-N,N-diallylaminophthalate prepared according to Example 4 are mixed together well and the mixture is heated to 165° C. with occasional stirring. A melt forms and this is poured into an aluminium mould, which has been preheated to 180° C., in order to produce sheets 4 mm and 2 mm thick. Curing is effected in a circulating air oven for 16 hours at 180° C. This gives transparent, bubble-free castings, the properties of which are indicated in Table I which follows.

EXAMPLES 10 and 11

Further castings are produced by the procedure described in Example 9. The molar ratios of the mixing components used, the curing conditions and the properties of the resulting castings are summarised in Table I.

EXAMPLES 12 and 13

12.89 g (0.036 mol) of 4,4'-bis-maleimidyl-diphenylmethane (BMDM) and 1.36 g (0.004 mol) of the diallyl 3-N,N-diallylaminophthalate prepared according to Example 1 are mixed well together and the mixture is heated to 155° C. with occasional stirring. A melt of low viscosity forms after 6 minutes and this is kept at 155° C. for a further 6 minutes (pre-crosslinking). The gelled mixture which has formed at the end of this period is allowed to cool and is ground to a fine powder. For processing by the compression moulding process, this powder is introduced into a compression mould for circular sheets, which has been pre-heated to 250° C., and is subjected to compression moulding at this temperature for 20 minutes under a pressure of 350 kp/cm². A transparent, firm sheet is obtained. The electrical properties of the compression moulded sheets are given in Table II.

A further compression moulded sheet is produced by the procedure described above. The molar ratio of the mixing components used, the pre-crosslinking and processing conditions and the electrical properties of the resulting compression moulded sheet are also given in Table II which follows.

A lengthening of the pot life by about 60% is achieved by the addition of about 10 mol % of an allyl compound to the bis-imide.

210°–215° C., and subjected to compression moulding at 210°–215° C. for 60 minutes under a pressure of 450 kp/cm². Transparent, firm sheets are obtained.

The 4,4'-bis-(3-maleimidyl-phthalimido)-diphenylmethane used in the above example can be prepared as follows:

91.89 g (0.378 mol) of 3-maleimidyl-phthalic anhydride (prepared by reacting 3-aminophthalic acid with maleic anhydride and subjecting the resulting 3-maleamidyl-phthalic acid to cyclisation with anhydrous sodium acetate and acetic anhydride, according to German Offenlegungsschrift No. 2,459,673) are dissolved in 343 ml of anhydrous DMA under a nitrogen atmosphere in a sulphonation flask and the solution is cooled to 0°–5° C. A solution of 35.68 g (0.18 mol) of 4,4'-diaminodiphenylmethane in 200 ml of DMA is then allowed to run in dropwise, with stirring, and, after the addition is complete, the reaction mixture is stirred for a further 2 hours at 20°–25° C. 132 ml (1.44 mols) of acetic anhydride are then added and the solution is heated to 80° C. for 2 hours, with stirring. After cooling to about 20°–25° C., the reaction product is precipitated with water. The resulting precipitate is filtered off, washed several times with water and dried for 20 hours at 80° C. in a vacuum cabinet. The reaction product is then boiled in approximately 10 times the amount by weight of ethanol for 20 minutes and the mixture is then filtered hot. After drying the product at 80° C. under a Table I

| Example No. | Phthalimide according to Example No. | Molar ratio Phtalimide | Molar ratio BMDM | Coring conditions | Flexural strength N/mm² 1) | Deflection mm 2) | Absorption of water 4 days 23° C in % 3) | tgδ × 10² (50 Hz) at 200° C 4) | tgδ × 10² (50 Hz) at 240° C 4) | ε(50 Hz) at 180° C 5) | ε(50 Hz) at 250° C 5) |
|---|---|---|---|---|---|---|---|---|---|---|---|
| 9 | 4 | 1 | 9 | 16 hours/180° C | | | | 0.60 | 1.38 | 3.4 | 3.3 |
| 10 | 5 | 1 | 9 | 16 hours/180° C | 64 | 1.7 | 1.0 | | | | |
| 11 | 5 | 2 | 8 | 16 hours/180° C | 63 | 1.9 | 1.4 | | | | |

Table II

| Example No. | Phthalimide according to Example No. | Molar ratio Phthalimide | Molar ratio BMDM | Pre-crosslinking conditions | Compression moulding conditions | tgδ × 10² (50 Hz) at 180° C 4) | tgδ × 10² (50 Hz) at 250° C 4) | ε(50 Hz) at 180° C 5) | ε(50 Hz) at 250° C 5) |
|---|---|---|---|---|---|---|---|---|---|
| 12 | 1 | 1 | 9 | 12 minutes/155° C | 20 minutes/250° C | 0.22 | 0.27 | 3.2 | 3.2 |
| 13 | 1 | 3 | 7 | 34 minutes/155° C | 25 minutes/240° C | 0.28 | 0.41 | 3.4 | 3.4 |

1) Flexural strength according to VSM 77,103
2) Deflection according to VSM 77,103
3) Absorption of water, 4 days at 23° C
4) Dielectric loss factor tgδ according to DIN 53,483
5) Dielectric constant ε according to DIN 53,483
VSM = Verein Schweizerischer Maschinenindustrieller
DIN = Deutsche Industrie-Norm

EXAMPLE 14

5.19 g (0.008 mol) of 4,4'-bis-(3-maleimidylphthalimido)-diphenylmethane and 0.76 g (0.002 mol) of the 1-diallylamido-2-allyl 3-N,N-diallylaminophthalate prepared according to Example 5 are mixed together well and the mixture is heated to 200° C., with occasional stirring, and then kept at this temperature for 15 minutes. The reaction mixture is then cooled and the prepolymer which has solidified is ground to a fine powder. For processing by the compression moulding process, this powder is introduced into a compression mould for circular sheets, which has been preheated to high vacuum, this gives 107 g of 4,4'-bis-(3-maleimidyl-phthalimido)-diphenylmethane in the form of a slightly yellowish powder; melting point 190°–210° C.

What is claimed is:

1. A phthalic acid diester or ester-amide of the formula I

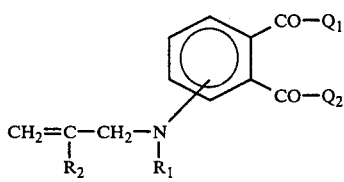  (I)

in which one of $Q_1$ and $Q_2$ is —$OR_3$ and the other is —$OR_4$ or

$R_1$ is hydrogen or

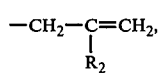

$R_2$ is hydrogen or methyl and $R_3$, $R_4$, $R_5$ and $R_6$ independently of one another are alkyl having 1–12 carbon atoms or alkenyl having 2–5 carbon atoms.

2. A phthalic acid diester or ester-amide of the formula I according to claim 1, in which $R_1$ is —$CH_2CH$=$CH_2$, $R_2$ is methyl or hydrogen and $R_3$ and $R_4$ are each alkyl having 1-8 C atoms or allyl, or $R_3$, $R_5$ and $R_6$ independently of one another are alkyl having 1–4 C atoms or allyl.

3. A process for the preparation of a phthalic acid diester or ester-amide of the formula I according to claim 1, wherein a compound of the formula II

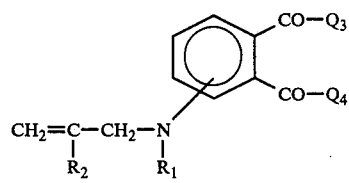  (II)

is reacted in the presence of an inorganic or organic base with an alcohol of the formula III

HO—$R_4$   (III)

to give a compound of the formula IV

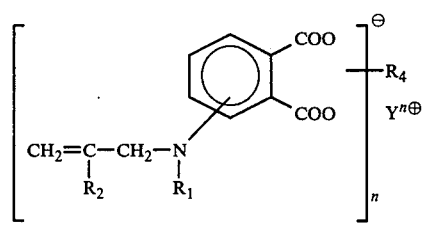  (IV)

and the compound of the formula IV is then allowed to react with an amine of the formula V

  (V)

and/or a compound of the formula VI

X—$R_3$   (VI)

in which formulae $R_1$, $R_2$, $R_3$, $R_4$, $R_5$ and $R_6$ are as defined in claim 1, one of $Q_3$ and $Q_4$ is —OH and the other is —OH or —$O^-M^+$, or $Q_3$ and $Q_4$ together are the grouping —O—, Y is the cation of an inorganic or organic base, X is a chlorine or bromine atom or the grouping —O—$SO_2$—O—$R_3$, $M^+$ is an alkali metal cation, a trialkylammonium cation having 3–24 carbon atoms or a quaternary ammonium cation and $n$ is the number 1 or 2.

4. A process according to claim 3, wherein a compound of the formula II is used in which $Q_1$ and $Q_2$ together form the grouping —O—.

5. A hot-curable mixture which is stable on storage and contains (a) at least one phthalic acid diester or one phthalic acid ester-amide of the formula I according to claim 1, (b) at least one polyimide which has, per molecule, at least two radicals of the formula XI

  (XI)

in which A is a divalent radical containing a carbon-carbon double bond, and, if appropriate, (c) a polymerization initiator.

6. A hot-curable mixture which is stable on storage, according to claim 5, which contains, as component (b), a bisimide of the formula XII

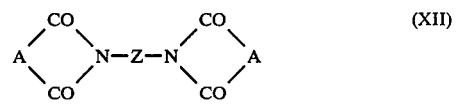  (XII)

in which Z is a divalent bridge member having 2–30 carbon atoms, A is —CH=CH—,

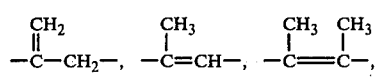

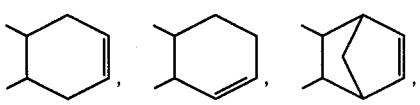

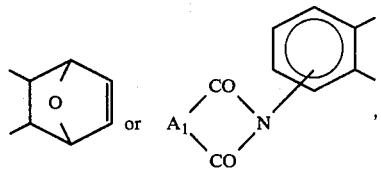

in which $A_1$ can have one of the meanings mentioned above for A.

7. A process for the preparation of a crosslinked polymer containing imide groups, wherein at least one phthalic acid diester or one phthalic acid ester-amide of the formula I according to claim 1 and at least one polyimide which contains, per molecule, at least two radicals of the formula XI

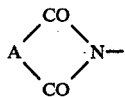
(XI)

in which A is a divalent radical containing a carbon-carbon double bond, are reacted with one another, if appropriate in the presence of a polymerization initiator.

8. A compound according to claim 1, of the formula

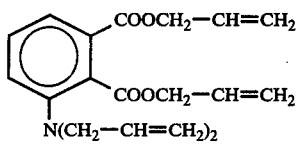

9. A compound according to claim 1, of the formula

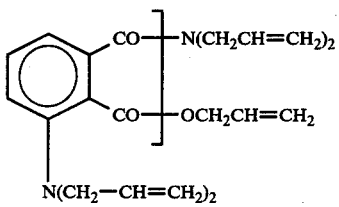

10. A compound according to claim 1, of the formula

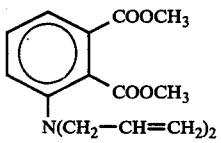

11. A compound according to claim 2 wherein $R_2$ is hydrogen and $R_3$ and $R_4$ are each alkyl having 1–4 C atoms or allyl.

* * * * *